United States Patent [19]

De Rigal et al.

[11] Patent Number: 4,682,608

[45] Date of Patent: Jul. 28, 1987

[54] APPARATUS FOR MEASURING VISCOELASTIC PROPERTIES OF SKIN IN VIVO

[75] Inventors: Jean P. De Rigal, Claye Souilly; Jean-Luc M. Leveque, Le Raincy; Laurent B. Rasseneur, Thorigny S/Marne; Marie-Jeanne Losch, Stains, all of France

[73] Assignee: "L'Oreal", Paris, France

[21] Appl. No.: 881,572

[22] Filed: Jul. 2, 1986

Related U.S. Application Data

[63] Continuation of Ser. No. 648,690, Sep. 10, 1984, abandoned.

[30] Foreign Application Priority Data

Sep. 13, 1983 [FR] France ............................... 83 14548

[51] Int. Cl.[4] ............................................... G10N 3/38

[52] U.S. Cl. ....................................... 128/774; 73/579

[58] Field of Search ................. 73/579, 653, 654, 655; 128/774, 335

[56] References Cited

U.S. PATENT DOCUMENTS

| | | | |
|---|---|---|---|
| 3,872,443 | 3/1975 | Ott | 128/774 |
| 4,177,798 | 12/1979 | Leveque et al. | 128/774 |
| 4,185,503 | 1/1980 | Saito | 73/653 |
| 4,295,374 | 10/1981 | Kusy | 73/579 |
| 4,297,884 | 11/1981 | Leveque et al. | 128/774 |
| 4,396,025 | 8/1983 | De Rigal et al. | 128/774 |
| 4,441,363 | 4/1984 | Hill et al. | 73/579 |

OTHER PUBLICATIONS

Biological System Transfer-Function Extraction Using Swept-Frequency and Correlation Techniques, by W. Williams et al.; Med. & Biol. Eng., vol. 10, #5; pp. 609-619.

"In Vivo Determination of Mechanical Properties of the Human Ulna by Means of Mechanical Impedance Tests . . ." by G. Thompson et al., Med. & Biol. Eng., vol. 14, #3, pp. 253-262.

An Apparatus for Measuring the Recoil Characteristics of Human Skin in Vivo, by C. Gunner et al., Med. & Biol. Eng. & Comput., 1979, pp. 142-144.

*Primary Examiner*—Lee S. Cohen
*Assistant Examiner*—David Shay
*Attorney, Agent, or Firm*—Cushman, Darby & Cushman

[57] ABSTRACT

Apparatus for measuring the Young's modulus or the internal damping coefficient of skin, for example human skin, in vivo, comprises a rectangular frame of non-metallic material to be adhered by means of double-sided adhesive tape to the surface of skin to be tested, and a movable assembly also adherable to the skin surface by means of tape.

The frame carries a vibration exciter in the form of a coil co-operating with a magnetic bead on the movable means, and also an opto-electronic movement sensor comprising an optical transmitter and receiver mounted next to one another on the frame and an optical reflector on the movable means for reflecting back to the light receiver the beam emitted by the light transmitter.

The electronic circuit includes a frequency scanning low-frequency generator and means for recording the frequency and the vibration amplitude as measured by the sensor, to plot the amplitude against the frequency for determining the resonance frequency and other characteristics such as the width of the resonance peak at half-height.

7 Claims, 4 Drawing Figures

APPARATUS FOR MEASURING VISCOELASTIC PROPERTIES OF SKIN IN VIVO

This is a continuation of application Ser. No. 648,690 filed Sept. 10, 1984 which was abandoned upon the filing hereof.

The present invention relates to an apparatus for measuring in vivo at least one of the viscoelastic properties, such as the internal damping coefficient and Young's modulus, of skin, and in particular human skin.

It is known that it is very useful to be able to measure the viscoelastic properties of skin for the study of the behaviour, and modifications of the behaviour, of skin, and in particular of human skin, before or after treatment, or to measure the efficiency of cosmetic preparations.

From French Patent No. 2,435,029, a process is known for measuring at least one mechanical property of an elastic material, in particular a ductile material of low hardness; this process is intended particularly for measuring the elastic properties such as Young's modulus and the internal damping coefficient of biological materials such as skin, hair and fur, vegetable or animal fibres, collagen fibres, and some relatively soft polymers. This process consists in subjecting a region of the material to be tested to a sustained vibration, determining the resonance frequency of the system subjected to the vibration with the material to be tested arranged so as to modify the resonance phenomenon of a mechanical resonator, and then deducing from the change in this resonance phenomenon at least one elastic property of the material tested. More precisely, the process described in this patent consists in arranging the region of the material to be tested between a vibrating component and a fixed component, subjecting this region of material to a sustained vibration in parallel to the said region, and then determining the resonance frequency of the system subjected to the vibration both in the presence and in the absence of the material to be tested, to deduce therefrom a viscoelastic property of this material. In a first embodiment, the region of the material to be tested, which is subjected to the vibration, is a region of skin, the measurement being carried out in vivo, while in a second embodiment of this process the region of the material to be tested which is subjected to the vibration is a specimen of skin stretched between the fixed component and the vibrating component, the measurement being carried out in vitro. According to a first alternative form, this process is carried out by frequency scanning in order to determine the resonance frequencies, but according to a second alternative form, a self-oscillator vibrating at the resonance frequency is produced by forming a control loop. This French Patent also proposes an apparatus which makes it possible to measure easily Young's modulus and/or the internal damping coefficient of a material such as skin by making use of the dynamic process which is the subject of this present Patent Application, and by deducing these viscoelastic properties from the resonance peak obtained with the apparatus. In the case when it is intended to measure Young's modulus, the region of material to be tested is arranged between the movable assembly and a fixed point, and the resonance frequencies of the mechanical vibration of the movable assembly are measured, with and without insertion of the region of material to be tested. To determine the resonance frequency of the movable assembly, whether or not associated with a region of skin to be tested, a frequency scan can be carried out by means of a variable frequency generator by recording the amplitudes of vibration as a function of the frequency, in order to determine the resonance peak the top of which is produced at the resonance frequency. However, to make the measurement automatic, it is also proposed to combine with the movable vibrating assembly an electronic circuit making it possible, using a feedback loop, to produce an electromechanical self-oscillator, the system vibrating automatically at the resonance frequency in this case. To do this, the movable assembly incorporates an electromagnetic coil and the amplitudes of vibration are determined by a photoelectric cell the output signal of which is sent to the coil input after passing through a controlled-gain amplifying system.

In the case where it is intended to measure the internal damping coefficient of the material to be tested, the resonance peak corresponding to the vibration of the movable assembly is recorded, and it is possible to deduce from the width of this peak at half-height the value of the internal damping coefficient, by means of a known mathematical relationship.

To carry out these various measurements, the above-mentioned French Patent proposes an apparatus comprising:

a movable assembly intended to be releasably integrally fixed to a region of skin to be tested, a base carrying an electromagnetic exciter intended to subject the movable assembly and the region of skin to a sustained vibration relative to the base, substantially in parallel with the region of skin to which the movable assembly is integrally fixed, an electronic circuit incorporating a device for feeding the electromagnetic exciter with low frequency current, and a proximity sensor which detects the vibrations of the movable assembly and which produces a signal image of these vibrations, and a device for displaying and/or recording the change in the signal image as a function of the exciter supply frequency, in order to determine the resonance frequency of the system subjected to the sustained vibration and to deduce therefrom at least one viscoelastic property of skin.

However, such apparatus permits, advantageously only in vitro use because the base is a fixed frame carrying, on the one hand, the movable assembly which is caused by the exciter to vibrate relative to the frame and which is integrally fixed to a member for fixing the region of skin to be tested and, on the other hand, a hooking member, the region of skin to be tested being arranged between the hooking member and the fixing member, which implies that the region of skin to be tested is a skin specimen previously taken from a subject.

The aim of the present invention is to offer a measuring apparatus making it possible in a simple manner to carry out in vivo the known process for measuring viscoelastic properties of skin, and in particular of human skin.

To this end, the present invention provides apparatus for measuring in vivo at least one viscoelastic property of skin, such as Young's modulus or the internal damping coefficient, the said apparatus comprising: a movable assembly, intended to be integrally fixed to a region of skin in a removable manner; a base carrying an electromagnetic exciter intended to subject the movable assembly and the region of skin to a sustained vibration relative to the base and substantially parallel to the region of skin to which the movable assembly is integrally fixed; an electronic circuit incorporating a device for feeding the electromagnetic exciter with low-frequency current, and a proximity sensor which detects the vibrations of the movable assembly and produces an image signal of these vibrations; a device for displaying and/or recording the change of the image signal as a function of the exciter feed frequency, in order to determine the resonance frequency of the assembly subjected to the sustained vibration, and to deduce therefrom at least one viscoelastic property of skin; wherein the base is a guard formed by a frame of a nonmagnetic material which is intended to be removably fixed on the skin by virtue of a double-sided adhesive tape whereby the skin bounded within the frame is the region of skin to be subjected to the sustained vibration; wherein the movable assembly incorporates within the frame a vibrating mass intended to be fixed to one face of a double-sided adhesive tape intended to have its other face fixed on the skin; and wherein the vibrating mass further carries a bead of a magnetic material which is positioned for co-operating with the exciter when the adhesive tapes are fixed to the skin and the guard and the vibrating mass are fixed on the adhesive tapes.

Such an apparatus makes it possible to pull, by means of vibrations of a very low amplitude parallel to the skin itself, the region of skin bounded by the guard frame and thus to excite preferentially the surface layers of the skin, that is to say the corneous layer, using the known vibratory process for measuring viscoelastic properties of human skin. The mechanical vibration induced in the vibrating mass by the co-operation between the bead of magnetic metal and the electromagnetic exciter is transmitted to the region of skin bounded within the frame by the vibrating mass and by the part of the doublesided adhesive tape which adheres to the skin and to which the vibrating mass itself adheres.

Preferably, as in said French Patent No. 2,435,029, the proximity sensor is an optoelectronic sensor but according to a characteristic specific to the present invention this sensor incorporates (a) an electro-luminescent transmitter and a photoelectric receiver which are carried by the guard, and (b) an optical reflector carried by the vibrating mass and reflecting the light beam received from the electro-luminescent transmitter towards the photoelectric receiver when the reflector vibrates with the vibrating mass.

In such a design the main part of the sensor, and all of the electromagnetic exciter which incorporates at least one electromagnetic coil, are carried by the guard with the advantage that the weight of the movable assembly, and consequently its inertia, can be restricted to the minimum useful values, and this favours good operation of the apparatus.

Advantageously, the electromagnetic exciter is arranged between the proximity sensor and the guard, in order to ensure pulling of the region of skin which is maintained, as much as possible, parallel to the guard.

In a simple embodiment, the vibrating mass comprises a plate for fixing to the double-sided adhesive tape and at least one upright integrally fixed to the fixing plate, this upright carrying the bead of magnetic metal and the optical reflector. The guard is a rectangular frame made of an aluminium alloy known as "Dural".

Preferably, as is known from the above-mentioned French Patent, the sustained vibration is driven by a low-frequency generator with frequency scanning, which feeds the exciter through a low-frequency amplifier. The opto-electronic sensor transmits the image signal to an a.c. voltmeter, and the output signal of the low-frequency generator is transmitted to the input of a frequency-voltage converter whose output signal, together with that of the a.c. voltmeter, are received by a recorder which produces the curve of the amplitude of the vibration of the movable assembly as a function of the frequency; this makes it possible to obtain the resonance peak and consequently, as described above, the resonance frequency at the maximum point of the curve, and the width of the peak at half-height, in order to deduce therefrom Young's modulus and the internal damping coefficient.

However, the low-frequency amplifier feeding the exciter may be an impedance-matching amplifier, and the opto-electronic sensor delivers the image signal to a phase-locking amplifier which also receives a reference signal from the low-frequency generator and has its output signal compared with the output signal of the low-frequency generator by a phase meter in order to detect the phase shift between the excitation and the motions of the movable assembly, and consequently the damping by the skin. This design has the advantage of permitting synchronous detection which eliminates the noise due to the inopportune movements of the subject and, moreover, it permits viscoelastic properties of skin to be studied completely.

If the intention is to determine merely the resonance frequency of the skin, it is preferable, as is known from the above-mentioned French Patent, to employ an apparatus forming a self-oscillator loop by means of a low-frequency amplifier feeding the electromagnetic exciter, and an automatic gain-control device receiving the image signal transmitted by the opto-electronic sensor, the output signal of the gain-control device being transmitted to the low-frequency amplifier so that the loop circuit, thus formed by reintroducing into the exciter the signal produced by the sensor, vibrates at the resonance frequency.

Finally, it is preferable that the apparatus incorporates, in both the above-mentioned versions, a frequency meter measuring the frequency of the current feeding the electromagnetic exciter.

An apparatus of this kind makes it possible to measure viscoelastic properties of human skin in vivo, before and after treatment, so that the effect of a cosmetic preparation can be appreciated quantitatively.

Furthermore, by altering the various operating parameters of this apparatus, such as the amplitude of the sustained vibration, the surface area of the region of skin bounded by the guard, and the mass of the movable assembly caused to vibrate on the subject, it is possible to study the layers of the skin to a greater or lesser depth.

In order that the present invention may be better understood a description will now be given, by way of illustrative examples, of one embodiment and an alternative form both shown in the attached drawings, in which.

Figure 1:
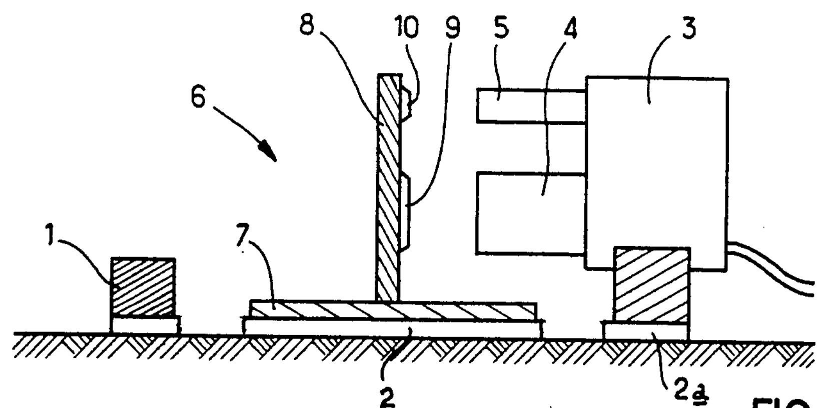
FIG. 1 shows schematically, partly in section and partly in elevation, the mechanical arrangement of a measuring apparatus according to the invention.

With reference to FIG. 1, it can be seen that the measuring apparatus incorporates a guard 1 formed by a rectangular frame of square cross-section, made of an aluminium alloy known as "Dural", which lies flat and adheres on the upper face of a double-sided adhesive tape *2a* which is rectangular and has the same surface area as the guard 1. The guard carries, through the intermediary of a base 3 fixed integrally on the rectangular frame, an electromagnetic exciter 4 overhanging the inside of the frame and incorporating an electromagnetic coil which is supplied with low-frequency alternating current and has its axis running parallel to the plane of the frame and at right angles to the side of the frame carrying the exciter 4. Above the exciter 4 the base 3 carries, also overhanging the inside of the frame, an opto-electronic sensor 5 consisting of a light transmitter, such as an electro-luminescent diode, and a photoelectric receiver, which adjoin each other. The apparatus also incorporates a movable assembly 6 fitted inside the frame 1. This movable assembly 6 consists of (a) a vibrating mass shaped as a fixing plate 7 carrying a mounting 8, perpendicular to the plate 7, (b) an armature in the form of a bead 9 made of a magnetic metal, and (c) an optical reflector 10. The fixing plate 7 is rectangular, and its width and its length are smaller than the width and the length respectively of the rectangular surface enclosed by the inner edge of the frame 1. The plate 7 has its lower face adhered to the upper face of a double-sided adhesive tape 2, which has the same surface area as the plate 7. The bead 9 and the optical reflector 10 are fixed above each other on the mounting 8. The bead 9 is arranged facing the electromagnetic exciter 4, parallel to the free end face of the exciter, and in a position for co-operating with it. The optical reflector 10 is arranged facing the opto-electronic sensor 5 in order to reflect the light beam, which it receives from the electro-luminescent transmitter, towards the photoelectric receiver.

As a result, after the assembly has been fixed on the skin by means of the double-sided adhesive tape 2 and *2a*, the alternating current supply to the exciter 4 sets the movable assembly and the region of skin bounded within the guard 1 into vibration with a low amplitude, by virtue of the presence of the bead 9 and the connection of the plate 7 to this region of skin by means of the adhesive tape 2. The flexibility of this removable connection to the skin, together with the relative locations of (a) the bead 9, on the mounting 8 which extends at right angles to the plate 7 for fixing to the skin, and (b) the exciter 4, makes it possible to subject the movable assembly 6 and the region of skin which is integrally connected to it to a vibration which is sustained, relative to the guard 1, and which is substantially parallel to this region of skin. The opto-electronic sensor 5, co-operating with the optical reflector 10, makes it possible to detect the frequency and/or the amplitude of these excitations which, as they take place parallel to the plane of the skin, makes it possible to excite the surface skin layers preferentially. The sensor 5 produces a signal which is an image of the vibrations of the movable assembly 6 and of the skin, without the operation of the exciter 4 being affected by the presence of the metal guard frame 1, since the "Dural" alloy from which the guard is made is non-magnetic.

Figure 2:
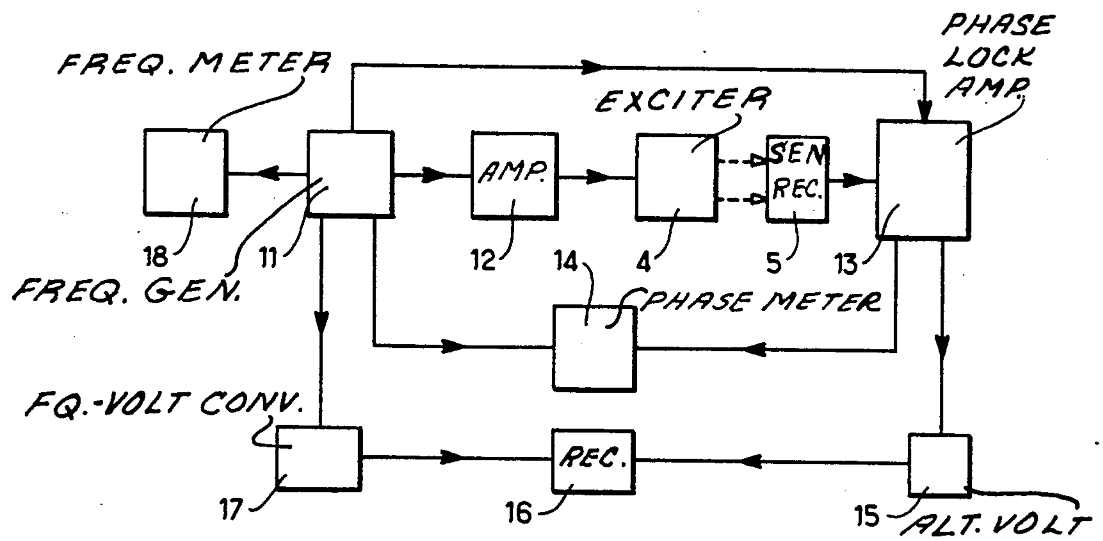
FIGS. 2 and 3 show respectively the general layout of the electronic circuit of a first and a second example of apparatus according to the invention, incorporating the mechanical arrangement of FIG. 1.

In a first example of an apparatus, the general diagram of which is shown in FIG. 2, the electronic circuit associated with the assembly shown in FIG. 1 incorporates a frequency scanning low-frequency generator 11 having a variable frequency of from 0.2 Hz to 2 kHz, and preferably from 10 to 100 Hz, feeding the electromagnetic exciter 4 through the intermediary of an impedance-matching amplifier 12, which ensures impedance-matching between the high impedance output of the generator 11 and the low impedance input of the electromagnetic coil of the exciter 4. The alternating image signal emitted by the sensor 5 is transmitted to an input of a phase-locking amplifier 13 which receives via a second input a reference signal produced by the low frequency generator 11. This phase-locking amplifier 13 provides signal amplification solely at the frequency emitted by the low-frequency generator 11, so as to permit synchronous detection and to eliminate the noise due to the inopportune motions of the subject on whose skin the apparatus is fixed. A first output of the phase-locking amplifier 13 is connected to an input of a phase meter 14 the other input of which receives the output signal of the low-frequency generator 11. The phase meter 14 thus makes it possible to measure the phase shift between the excitation and the motion of the movable assembly 6, and consequently to calculate the damping by the skin. In parallel, a second output of the phase-locking amplifier 13 is connected to an alternating voltmeter 15, the output of which is connected to a recorder 16 which receives via a second input the output signal of a frequency-voltage converter 17 whose input receives the output signal of the low-frequency generator 11. The recorder 16 plots the curve giving the amplitude of the vibrations of the movable assembly 6 as a function of the excitation frequency. This curve makes it possible to acquire several parameters, particularly the resonance frequency which corresponds to the frequency at the top of the resonance peak of this curve, and the width of the resonance peak at mid-height, these two data making it possible to calculate Young's modulus and the internal damping coefficient, as already mentioned earlier.

This first example of an apparatus permits, therefore, a relatively complete investigation to be made of the viscoelastic properties of skin, by virtue of the frequency drive of the sustained vibration.

Figure 3:
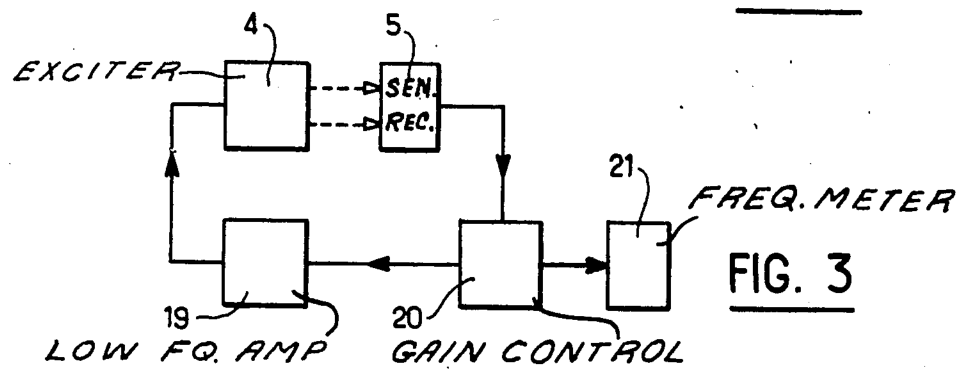

Finally a frequency meter 18, connected to the output of the low-frequency generator 11, makes it possible to monitor the frequency scanning provided by the generator. When the intention is merely to determine the resonance frequency, in order to calculate Young's modulus, the apparatus whose general diagram is shown in FIG. 3 may be employed. In this apparatus the electronic circuit incorporates a low-frequency amplifier 19 for feeding the exciter 4. The sensor 5 transmits its output signal, which is a signal image of the frequency of vibration of the movable assembly 6, to an automatic gain-control device 20. The latter, with its output signal transmitted to a frequency meter 21, is also connected to the low-frequency amplifier 19 into which it reintroduces the signal originating from the sensor 5 in order to feed the exciter 4. There is thus formed a circuit looped as a self-oscillator which vibrates at the resonance frequency which can be read off on the frequency meter 21.

Figure 4:
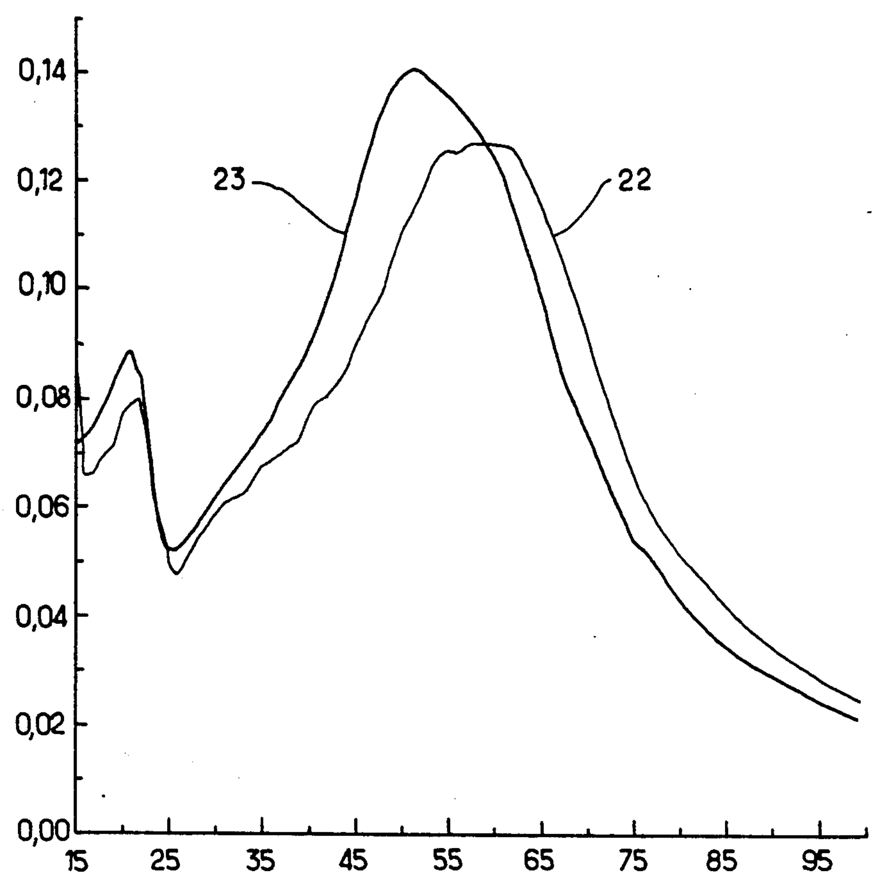
FIG. 4 shows two experimental curves giving the amplitude of the vibrations as a function of the frequency, before and after a treatment on the skin.

An example of the use of these sets of apparatus, illustrating the potential applications, is described below with reference to FIG. 4, which shows the recorded resonance curves of human skin under the effect of a treatment with distilled water (pH=7).

The experiment was carried out on the inner side of the forearm of a male subject aged 30. A first recording (curve 22) of the amplitude as a function of frequency was produced, before the treatment, with the aid of an apparatus according to FIGS. 1 and 2 fitted with a movable assembly 6 weighing 7 g. Next, 2 $cm^3$ of distilled water were applied for 2 minutes on the region of skin in question of the inner side of the subject's forearm. At the end of this period, excess water was sponged off and then a second recording of the curve of amplitude as a function of the frequency (curve 23) was produced with the aid of the same apparatus, 15 minutes after the treatment.

The interpretation of these curves 22 and 23 has made it possible to complete the following table, which relates to the effects of an application of distilled water on the viscoelastic properties of human skin in vivo.

| | Resonance Frequency | Damping | Amplitude at Resonance (Root Mean Square) |
|---|---|---|---|
| before treatment | 60 Hz | 0.208 | 0.127 V |
| 15 minutes after treatment | 52 Hz | 0.212 | 0.14 V |

The effect of distilled water on the viscoelastic properties of skin is shown by the shift in the resonance frequency, and by the change in the damping and in the amplitude at resonance. These parameters make it possible to quantify the effectiveness of the treatment.

When the curves 22 and 23 are re-examined, it is also possible to note the presence of secondary peaks, which appear as shoulders on the main resonance peak.

The effectiveness of a cosmetic treatment on human skin can thus be determined by virtue of the measurement in vivo, obtained using sets of apparatus according to the invention, of various physical parameters which indicate the effect of products on the elasticity of viscosity of human skin.

It is clearly understood that the sets of apparatus described above can lead to any desirable modification, without departing thereby from the scope of the invention as defined by the claims.

We claim:

1. In apparatus for measuring in vivo at least one viscoelastic property of skin in a region of the skin, the said apparatus comprising:

(a) a movable assembly;

(b) means for fixing the movable assembly to the region of skin to be tested;

(c) a base;

(d) an electromagnetic exciter carried by said base and intended to subject the movable assembly and the region of skin to a sustained vibration relative to the base in a direction substantially parallel to the region of skin to which the movable assembly is to be fixed;

(e) an electronic circuit incorporating means for feeding the electromagnetic exciter with low-frequency current, and a proximity sensor for detecting the vibrations of the movable assembly and for producing an image signal of these vibrations;

(f) means for displaying and/or recording the change of the image signal as a function of the exciter feed frequency, in order to determine the resonance frequency of the assembly subjected to the sustained vibration, and to deduce therefrom at least one viscoelastic property of skin;

the improvement wherein:

(g) the base is a guard formed by a frame of a nonmagnetic material, said frame extending in a plane and including a side, said electromagnetic exciter including an electromagnetic coil having an axis extending parallel to said plane of said frame and perpendicular to said side of said frame, said side of said frame supporting said electromagnetic exciter;

(h) said fixing means include double-sided adhesive tape for fixing the frame removably on the skin whereby the skin bounded within the frame in the region of skin to be subjected to the sustained vibration;

(i) the movable assembly including a vibrating mass intended to be fixed within the frame;

(j) the fixing means further include further double-sided adhesive tape having one face adhered to said vibrating mass and the other face adapted to be adhered on the skin to be measured; and (k) the vibrating mass further carries a bead of a magnetic material which is positioned for co-operating with the exciter when the first mentioned and further double-sided adhesive tapes are fixed to the skin and the guard and the vibrating mass are fixed on the tapes;

said vibrating mass incorporating (a) a plate fixed to the double-sided adhesive tape, and (b) at least one mounting fixed to the plate said mounting extending substantially perpendicular to said plate and carrying said magnetic bead, and said frame enclosing an interior space and said electromagnetic exciter extending in overhanging relationship with a portion of said interior space of said frame.

2. Apparatus according to claim 1, wherein the proximity sensor is an opto-electronic sensor incorporating (i) an electro-luminescent transmitter and (ii) a photoelectric receiver carried by the guard and (iii) an optical reflector carried by the vibrating mass, and wherein said reflector vibrates with the vibrating mass, and reflects towards the photoelectric receiver the light beam which it receives from the electro-luminescent transmitter.

3. Apparatus according to claim 1, wherein the electromagnetic exciter is arranged between the proximity sensor and the guard.

4. Apparatus according to claim 1, wherein the proximity sensor is an opto-electronic sensor incorporating (i) an electro-luminescent transmitter and (ii) a photoelectric receiver carried by the guard and (iii) an optical reflector carried by the vibrating mass, and wherein said reflector vibrates with the vibrating mass, and reflects towards the photoelectric receiver the light beam which it receives from the electro-luminescent transmitter, and wherein the optical reflector is carried by the mounting.

5. Apparatus according to claim 1, wherein the guard is a rectangular frame of a nonmagnetic aluminum alloy.

6. Apparatus according to claim 1, wherein the electronic circuit incorporates:

(i) a low-frequency amplifier for feeding the electromagnetic exciter;

(ii) an automatic gain-control device connected to the output of the proximity sensor, which sensor provides an image signal of the frequency of vibration of the movable assembly; and (iii) means connecting the output of the gain-control device to the input of the low-frequency amplifier so as to form, by looping, a self-oscillator vibrating at the resonance frequency.

7. Apparatus according to claim 1, wherein the electronic circuit incorporates a frequency meter for measuring the frequency of the current feeding the electromagnetic exciter.

* * * * *